United States Patent [19]
Voitik

[11] Patent Number: 5,106,300
[45] Date of Patent: Apr. 21, 1992

[54] DENTAL IMPLANT ATTACHMENT STRUCTURE AND METHOD

[76] Inventor: Anton J. Voitik, 72351 Sommerset Dr., Palm Desert, Calif. 92260

[21] Appl. No.: 588,661

[22] Filed: Sep. 26, 1990

[51] Int. Cl.$^5$ .............................................. A61C 8/00
[52] U.S. Cl. .................................................. 433/173
[58] Field of Search ................ 433/173, 174, 175, 176, 433/201.1

[56] References Cited

U.S. PATENT DOCUMENTS

| | | | |
|---|---|---|---|
| 4,744,756 | 5/1988 | Ross | 433/173 |
| 4,758,161 | 7/1988 | Niznick | 433/173 |
| 4,854,872 | 8/1989 | Detsch | 433/174 |
| 4,886,456 | 12/1989 | Ross | 433/173 |
| 4,906,191 | 3/1990 | Soderberg | 433/173 |

Primary Examiner—Cary E. O'Connor
Attorney, Agent, or Firm—Brown, Martin, Haller & McClain

[57] ABSTRACT

A dental implant attachment structure comprises an abutment member having a base end shaped for mating engagement with an upper coupling face of an implant member, the abutment member having a through bore and spaced inner and outer walls extending from its base end to form an internal chamber open at the opposite end of the member, a securing mechanism for extending through the bore to releasably secure the abutment member to an implant member, and an impression cap for releasably mounting on the open upper end of the abutment member to close the internal chamber. In one embodiment the securing mechanism comprises a single screw. The abutment member serves both as an impression transfer part for transferring the implant site to a laboratory cast, and also as part of the final laboratory manufactured restoration for installation at the implant site.

19 Claims, 3 Drawing Sheets

DENTAL IMPLANT ATTACHMENT STRUCTURE AND METHOD

BACKGROUND OF THE INVENTION

The present invention relates generally to attachment structures and methods for installing dentures or other prosthetic devices in the jaw, and is particularly concerned with a system for attaching a denture to a previously installed implant member in the jaw.

During normal procedures in preparing a dental implant supported restoration or denture, a dentist needs to transfer the implant location from the patient to a working cast, or laboratory model of the patient's jaw, accurately. To accomplish this, a dentist must use impression or implant location transfer parts which are specific to the implant system already in place in order to transfer the implant location to the working cast. The impression taken of the patient's jaw, with the transfer parts in place, serves as the "negative mould" for the working cast or laboratory model of the patient's jaw. Implant analogues must be held in place by the transfer parts while the cast is poured. The working cast is usually made from dental stone or synthetic dental stone. The procedure is complicated by the inherent volumetric and linear expansion of dental stone materials, the multitude of parts required per implant site, the play or loose fit of the parts against each other, the different qualities of the implant materials used, and the various possible, abnormal implant location sites in the patient's jaw. These problems result in inaccuracies arising in the working cast.

Since dental implants are more rigidly anchored in the jaw than are natural teeth, implant restorations or dentures must be made accurately and cannot be "teased" into place as an existing tooth supported dental restoration often is. Implant restorations must fit accurately and are secured in place usually via precision machined fixation screws rather than the dental cements used in standard crown and bridge restorations. The multiple parts needed both in the transfer procedure and subsequent denture attachment make this process both complex and relatively expensive.

SUMMARY OF THE INVENTION

It is an object of the present invention to provide a new and improved denture attachment system and method for use with implants embedded in a patient's jaw, which requires less parts and produces greater accuracy in the working cast.

According to one aspect of the present invention, a denture attachment structure or system is provided, which comprises an abutment member having an interface formation at one end for mating engagement with the upper mating end of an implant member installed in a patient's jaw, the abutment member being open at its opposite end and having spaced inner and outer walls defining an internal volume for receiving denture casting material, a securing device for releasably securing the abutment member to an implant member, and an impression cap for releasably securing to the open end of the abutment member to seal its internal volume during impression taking. Preferably, the securing mechanism includes a temporary securing device for securing the abutment member temporarily to an implant member during impression taking, and to a suitable implant analogue during working cast production, and denture casting, and a fixed securing device for permanently securing the abutment member and an attached denture cast around the abutment member to the implant member.

Preferably, the internal volume comprises an annular, elongate and generally V-shaped internal chamber extending from the base end towards the open upper end of the abutment member, and the impression cap has a corresponding, mating annular projection for extending into and filling the internal chamber during an impression taking step, so that impression material cannot enter the internal chamber. The impression cap also has an orientation marking for forming an orientation mark on the impression, to facilitate accurate transfer of the implant location.

The outer wall is preferably relatively thin and is capable of being machined or cut around its periphery to follow the gum line around the implant site, so that when installed the outer wall will form a transmucousal member level with the surrounding gum margin. Denture material is cast around the projecting upper portions of the abutment member as it is secured to the implant analogue in a working cast, and the resultant projecting base portion of the abutment member forms a customized gingival margin between the upper end of the implant member and the gum level surrounding the implant site. The outer surface of the abutment member in this region may be suitably treated if desired to provide denture matching color and tissue compatibility, for example.

The inner surface of the outer wall and opposing outer surface of the inner wall are preferably roughened or provided with grooves to produce a better attachment to the denture casting material used in forming the denture or restorative device. The extended internal volume will provide a strong attachment between the casting material and abutment member, reducing the risk of separation after extended use. The inner wall is of sufficient thickness to withstand high occlusal loads.

Because this system uses the same abutment member both as the impression transfer part for transferring the implant location to a laboratory made working cast, and as the securing device for securing the cast denture or restorative structure to the implant after laboratory manufacture, the number of parts required for implant dentistry is substantially reduced. The configuration is simple and uses a minimum of separate parts.

According to another aspect of the present invention, a method of manufacturing and installing a denture on one or more implant members implanted in a patient's jaw is provided, which comprises the steps of mating a matching, mating base end surface of an abutment member to a corresponding mating end of an installed implant member so that the abutment member projects upwardly through the gum, mounting an impression cap over an open upper end of the implant member to cover an internal volume in the implant member, securing the abutment member to the implant member, taking an impression of the patient's jaw around the implant site and attached abutment member and impression cap, releasing the abutment member from the implant member and removing the impression, abutment member and attached impression cap from the patient's mouth, attaching an analogue of the implant member to the base end of the abutment member; forming a working cast around the analogue and projecting portion of the abutment member, removing the impression and impression cap from the abutment member, forming a cast of the denture over the portion of the abutment member projecting from the working cast so that the cast material extends into the internal volume of the abutment member, releasing the abutment member and denture from the analogue, and securing the abutment member and attached denture to the implant member in the patient's jaw.

Alternatively, the cast denture may be formed separately from a wax pattern and then secured to the abutment member with dental cement.

Preferably, the step of initially securing the abutment member to the implant member is followed by a step of cutting down a projecting outer wall of the implant member to match the level of the gum surrounding the implant site. In this way, the abutment member is provided with a customized gingival margin extending from the implant member to the gum level surrounding the implant site.

The denture installation system and method for implant dentistry according to this invention is simpler and less expensive than conventional systems, and also improves accuracy in transfer of the implant site to the working cast. Odd tooth angles can easily be compensated, and the structure is easily disassembled for fine tuning work. It utilizes a minimum of parts, and can be provided in standard sizes and with mating abutment surfaces for all standard implant designs and sizes.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENT

Figures 1, 1A:
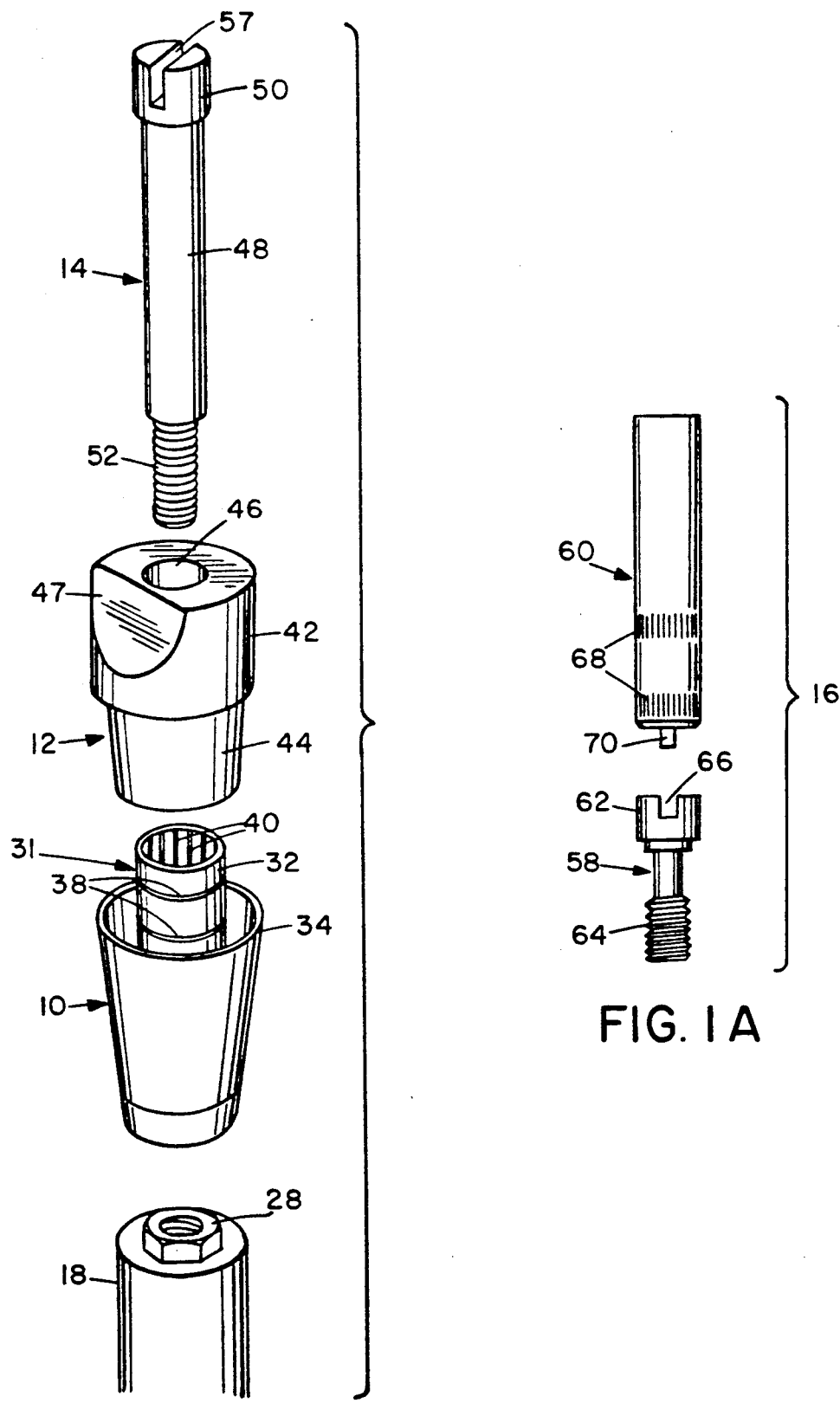
FIG. 1 is an exploded, perspective view of the various parts of an installation system for making and installing a denture or restorative structure on an implant previously implanted in a patient's jaw.
FIG. 1A illustrates the final fixation parts of the system.
Figure 2:
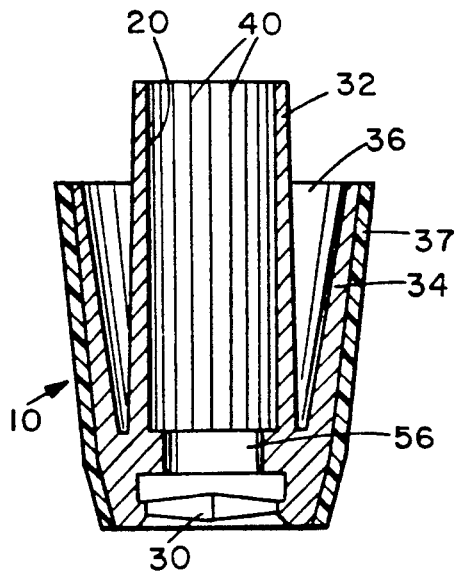
FIG. 2 is a cross sectional view of the abutment member of the system of FIG. 1.

FIGS. 1, 1A and 2 of the drawings illustrate the various parts of the denture implant attachment system according to a preferred embodiment of the invention. The system basically comprises an abutment member 10 which forms both the transfer device for transferring an implant location in the jaw to a working laboratory cast, and also part of the attachment for securing the cast denture or restorative device to the implant after laboratory work is complete, an impression cap 12 designed to be secured to the upper end of member 10 during part of the procedure, a first, temporary securing device 14 for securing the abutment member temporarily to the implant while an impression is taken, and a second, or final, securing mechanism 16 (see FIG. 1A) for securing the abutment member to the implant after casting the denture around it. Also illustrated in FIG. 1 is an analogue 18 of an implant member for use in the working cast as will be explained in more detail below.

In the embodiment illustrated in the drawings, the abutment member is designed for attachment to one particular type of existing implant member. However, it will be understood that it may be modified for attachment to other types of implant members in alternative embodiments, by suitable design of the abutment surface to match that of the implant member to which it is to be secured. Also, it will be understood that the parts will be made in a range of sizes corresponding to the range of implant member sizes.

The abutment member 10 is made of any suitably hard dental material, such as metals, synthetics or ceramics. In a preferred embodiment, this part is of titanium. The abutment member 10 comprises an elongate, generally cylindrical member having a central through bore 20, and a base end 22 of size and shape for mating engagement with the upper end 24 of an implant member 18, 26 to which it is to be secured. In the illustrated embodiment, the implant member is of a type having a projecting hexagonal boss 28. Thus, the base end 22 has a corresponding hexagonal indent 30 and an outer diameter matching that of the upper end of the implant member. A range of abutment members of diameter varying from around 3.00 to 8.50 mm is preferably provided, with the dimensions of the other parts of the system being also provided in a similar range. However, it will be understood that the base or abutment end 22 may alternatively be machined to fit over other types of implant devices.

Projecting from the base end 22 towards the upper, open end 31 of the abutment member is an inner cylindrical wall 32 surrounding bore 20, and an outer, flared skirt or wall 34 spaced from the inner wall to define an extended internal annular volume or chamber 36 of V-shaped cross-section which is open at its upper end. The opposing inner and outer surfaces of the outer and inner walls, respectively, preferably have retention grooves 38, and may also be roughened or textured to provide increased surface area for attachment to dental casting material, as explained in more detail below. The inner surface of inner wall 32 is provided with a series of elongate alignment grooves 40. The outer surface of outer wall 34 which will form the transmucousal segment of the finished denture or restorative device is preferably highly polished and smooth. If desired, it may be treated with any suitable enhancement materials for enhanced color and tissue compatibility. A slip cover or sleeve 37, illustrated in FIG. 2, is preferably provided for protecting this surface during laboratory work. The slip cover may be of any suitable semi-rigid or rigid synthetic material.

Figure 5:
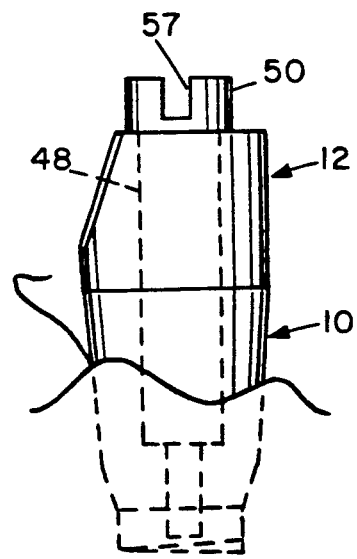
FIG. 5 is a side elevational view illustrating a subsequent step in the method.
Figure 6:
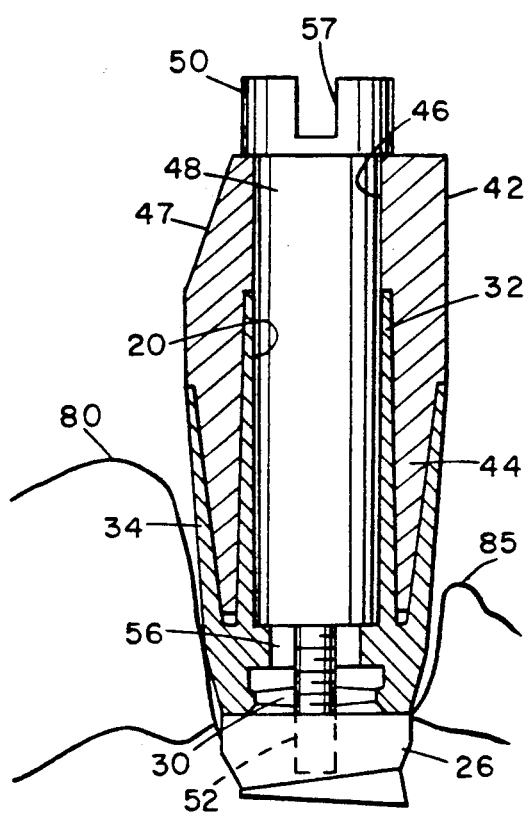
FIG. 6 is cross-sectional view through the parts assembled as in FIG. 5.

Impression cap 12 is designed to fit over the open upper end of the abutment member 10 as illustrated in FIGS. 5 and 6, and is preferably formed of synthetic material. Cap 12 has a generally cylindrical head 42 with a frusto-conical, annular projection 44 designed for mating engagement in the internal volume or chamber 36 of the abutment member, as best illustrated in FIG. 6. Cap 12 has a stepped through bore 46 having a diameter at its upper end matching that of the bore 20 in member 10, and at its lower end matching the outer diameter of wall 32, so that it is a close sliding fit over wall 32 as illustrated in FIG. 6. The head portion includes an anti-rotation, orientation flat or indent 47. Clearly any suitable anti-rotation surface could be used here, including a projection or differently shaped cut-out on the outer surface of head portion 42. The outer diameter of head portion 42 matches that of the outer wall of member 10, to produce a smooth transition as illustrated in FIG. 6. A suitable anti-rotation engagement will be provided between impression cap 12 and abutment member 10, for example the inner surface of bore 46 may be provided with elongate ribs for engagement with corresponding elongate grooves on the outer surface of inner wall 32, to prevent relative rotation between the parts and loss of the precise orientation of flat 47. These anti-rotation formations have been omitted from the drawings for reasons of clarity.

Figure 3:
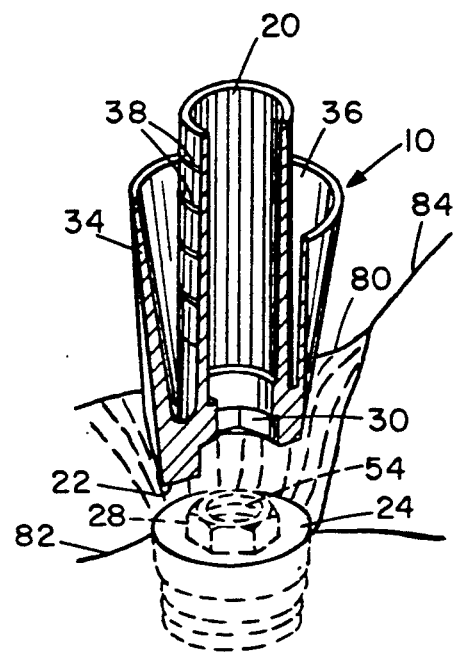
FIG. 3 is a partially cut away, perspective view showing a first step in a method of using the system of FIG. 1 according to a preferred embodiment of the invention, illustrating how the abutment member is attached to an upper end of an implant member.
Figure 7:
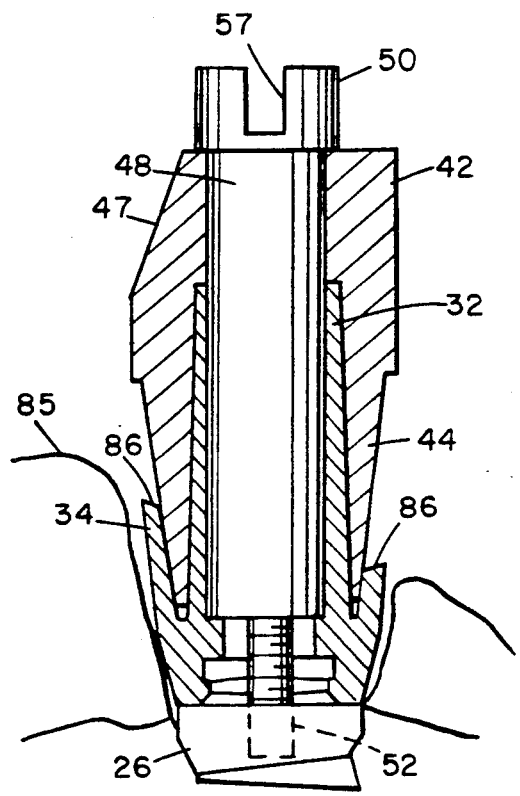
FIG. 7 illustrates another step in the method.

The temporary fixation screw 14 has an elongate head portion 48 with a slightly enlarged upper end 50 and a projecting, screw threaded shaft 52 designed for threaded engagement in a corresponding bore 54 in the upper end of implant member 26 (see FIG. 3). The bore 20 in abutment member 10 has an upper portion of diameter corresponding to that of the head portion 48 of screw 14, and a reduced diameter portion 56 leading into hexagonal indent 30 at the base end for receiving shaft 52. When the fixation screw 14 is inserted through the aligned bores in the impression cap 12 and abutment member 20, the enlarged upper end 50 will seat on the upper end of cap 12 while shaft 52 projects out of the base end of abutment member 10, as best illustrated in FIG. 7. An elongate removal slot or indent 57 is provided in the upper end of head portion 48.

The final fixation device 16 includes a shorter, final fixation screw 58 and an anti-rotation device 60 for preventing rotation of the fixation screw 58. The final fixation screw 58 has a short head portion 62 and an extending, threaded shaft portion 64 equivalent to shaft portion 52 of the temporary fixation screw 14. Both fixation screws may be of any suitably hard material such as metal or synthetics. A removal slot 66 is provided in the upper end of head portion 62. Anti-rotation device 60 comprises an elongate cylindrical member which is a close sliding fit in the upper portion of bore 20, and which has grooving or striations 68 on its outer surface for mating with the corresponding striations on the internal surface of bore 20 to resist rotation. A tab 70 extending from the lower end of member 60 is designed for engagement in slot 66. Device or member 60 may be of any suitably hard dental material such as metal, synthetics, or ceramics. This device also acts as an occlusal seal for the implanted denture or restorative device, as will be explained further below.

The implant member analogue 18 is used in the laboratory formed working cast of the patient's jaw and has an upper end contour matching that of the installed implant, and a screw threaded bore 88 of equivalent dimensions to bore 54. It may be of any suitable material as is conventionally used for such analogues.

Figure 10:
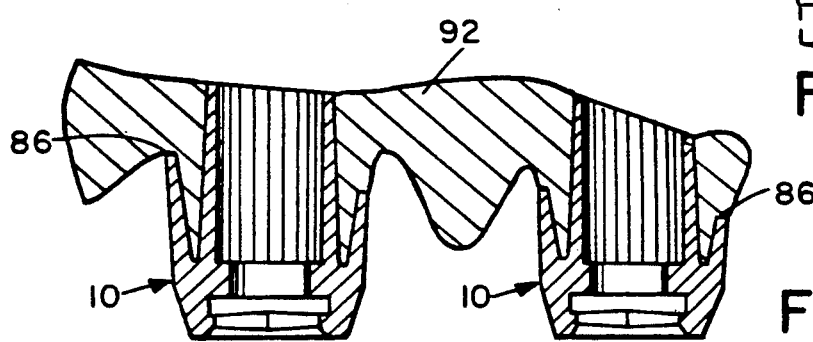
FIG. 10 illustrates use of the system for forming a restorative device for attaching to more than one implant site.

A method of using the kit or system described above in implant dentistry according to a preferred embodiment of the invention will now be described in more detail with reference to FIGS. 3 to 9 which illustrate a series of steps in the method. This description relates to the use of the parts in implantation of a single, free standing restoration at a single implant site in a patient's jaw. However, it will be understood that similar techniques may be used for multiple implant site restorations to install a larger dental restoration, for example as illustrated in FIG. 10 of the drawings.

Referring first to a single restoration or denture site, the parts illustrated in FIG. 1 are used in the implant location transfer procedure, in the laboratory construction of the restoration or denture device, and in installation of the device in the patient's jaw. FIG. 3 illustrates a typical implant site 80 in which an implant member 26 of a standard type has been implanted in the patient's jaw bone 82 with its upper coupling surface 24 substantially level with the bone. A cut out area in the gum 84 exposes the implant member. Once the implant member has been installed, it must be left for a certain time period for so-called osseo-integration, or bonding with the bone, to occur.

Figure 4:
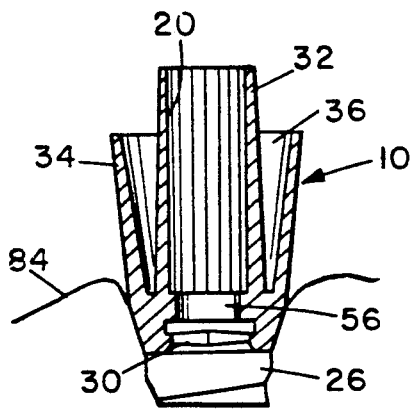
FIG. 4 is a cross-sectional view illustrating the abutment member mounted on the implant member.

The implant location or locations relative to the patient's jaw must be transferred to a laboratory working cast so that the denture or restoration can be made accurately. The abutment member 10 is therefore first mounted with its lower abutment face 22 in mating engagement with the upper coupling surface 24 of implant member 26, as illustrated in FIGS. 3 and 4. The impression cap 12 is then placed over the open upper end of the member 10, as illustrated in FIGS. 5 and 6, and the temporary fixation screw 14 is inserted through the aligned bores 46, 20 in the cap 12 and member 10, until the screw threaded shaft 52 is threadably engaged with a corresponding threaded bore 54 in the upper end of implant member 26, securing the impression cap and abutment member firmly in position.

In one clinical method, an impression is then made of the implant site using standard dental impression material in an impression tray inserted into the patient's mouth. With the impression material in place around the site, the temporary fixation screw is released, allowing the impression and abutment member to be removed with the impression tray. In order to retain the abutment member in its precise location in the impression, the implant analogue 18 is then preferably secured to the exposed end of the assembly, with projecting shaft 52 of screw 14 extending into a corresponding screw threaded bore 88 in analogue 18. In a second clinical method, the abutment member and impression cap may, if desired, be removed from the impression, since their location and orientation will be apparent from the impression of orientation flat 47 in the recess formed by the cap and abutment member in the impression material. The parts are then transported to a dental laboratory.

At the laboratory a working cast 84A of the patient's jaw can be made using the impression as well as the analogue 18 of the implant member. The abutment member with the impression cap in place are retained and precisely located in the corresponding indentation in the impression, and analogue 18 is located against the lower abutment face 22 of the member 10. The impression then acts as a mould while a suitable dental casting material, such as dental stone or synthetic dental stone, is poured into the impression. Once the material is set, it can be removed from the impression by releasing screw 14 from analogue member 18, retaining the or each implant analogue in a location in the resultant working cast which is equivalent to the corresponding implant site in the patient's jaw. During the casting procedure, the outer, polished surface of abutment member 34 may be protected with sleeve or cover 37.

Figure 8:
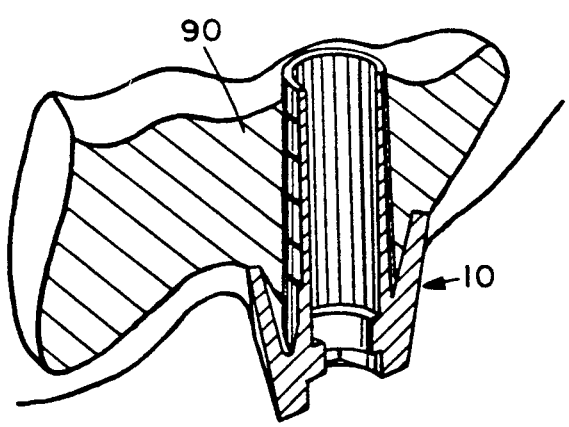
FIG. 8 illustrates a subsequent step in the method.
Figure 9:
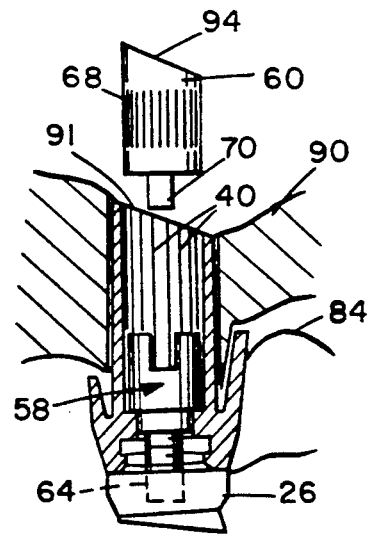
FIG. 9 illustrates a final step in which the abutment member and attached denture cast are secured to the implant member after laboratory work.

The abutment member and impression cap are then removed from the impression, and the abutment member alone is installed on the analogue 18, again securing it in place with temporary fixation screw 14. At this point the outer wall 34 of the abutment member is adjusted to follow the gingival or gum level 85 surrounding the implant site in the working cast 84A. This is done by cutting the wall 34 with a suitable cutting tool until its upper, cut edge 86 follows the gum line surrounding the implant site, as illustrated in FIG. 7. This allows accurate reproduction in the laboratory of the gingival or transmucousal margin, which takes into account any odd angles or orientations. The outer wall 34 is made thin enough to be cut relatively easily in this step. Preferably, the inner wall is thicker than the outer wall, although the thickness will depend on the actual material used. Denture material is then cast around the abutment member and suitably shaped to provide the desired denture or cast 90 for matching opposing tooth surfaces in the patient's jaw, as illustrated in FIG. 8. The casting material will extend into the internal volume 36 between the opposing inner and outer walls of the abutment member, and into the grooves 38, which assist in bonding the cast denture material to the abutment member and resist displacement as a result of occlusal loads. The projecting upper end of the inner wall 32 will be cut to produce a cut upper end 91 which matches the contour of the restoration or denture, as illustrated in FIG. 9. FIG. 10 illustrates a two implant site restoration 92 at this stage in the procedure. In an alternate procedure, the restorative structure or denture may be cast separately from the abutment member, using a wax pattern formed on the abutment and then separated by lifting it off. The restorative structure can then be cast from this pattern in a standard manner and subsequently cemented on the abutment member.

The abutment member and attached cast are now ready for installation in the patient's oral cavity. First, the abutment member is positioned at the correct orientation on the implant member so that the upper end of outer wall 34 follows the gum line. The final fixation screw is then inserted into the bore 20 with its threaded shaft 64 in threaded engagement with the bore 54 in member 26, as seen in FIG. 9. The rotation preventer or anti-rotation member 60 is then inserted into the cavity so that tab 70 engages slot 66. The upper end 94 of member 60 is machined down to match the contour of the restorative structure or cast 90, as illustrated in FIG. 9, and this member will be of a material colored to match that of cast 90. If desired, a suitable dental bonding material may be applied to the surface of member 60 prior to insertion so that it is firmly sealed in bore 20 when installed. However, this is preferably only used after a post-insertion adjustment period, ensuring that the cast fits and functions correctly in the mouth before it is bonded in place. Member 60 seals the bore 20 against ingress of food and other foreign materials, and at the same time acts to resist occlusal forces tending to rotate screw 58 and loosen it.

The denture or restorative structure can be quickly and cleanly removed from the mouth if additional work is needed without destroying the cast, and can be easily re-inserted after any necessary adjustment in its contour. This arrangement substantially reduces the number of parts needed for post-implantation implant dentistry procedures, and simplifies the impression taking, laboratory work, and fitting of casts onto existing implant sites considerably. This system also provides improved accuracy in the working cast, by rigidly fixing the implant transfer post or analogue during the pouring of the working cast, and eliminating free play between the parts during this procedure. The number of parts needed is reduced significantly by providing an impression transfer part which is also used as part of the final laboratory manufactured cast to be installed on the patient's jaw. The number of laboratory steps and the number of parts involved for completing the restoration is also significantly reduced, reducing the expense of restorative work. The gingival margin is customized to the level of the gum line, improving the appearance of the denture when installed. The abutment member is designed to have sufficient internal volume for receiving the casting material so that the assembled cast will resist separation as a result of occlusal loads. This arrangement eliminates stacking of parts and uses only one screw in each stage of the procedure. The same configuration of parts is used for all applications, including single and multiple unit restorations as well as odd angles, and fixed or removable designs. This structure can also be used for direct application of pre-manufactured resin teeth, eliminating the laboratory procedure, and for installation of temporary dentures, for example.

Although a preferred embodiment of the invention has been described above by way of example only, it will be understood by those skilled in the field that modifications may be made to the disclosed embodiment without departing from the scope of the invention, which is defined by the appended claims.

I claim:

1. A denture attachment system, comprising:
   an abutment member having a mating abutment surface at one, base end comprising means for mating engagement with the upper mating surface of an implant member installed in a patient's jaw, the abutment member being open at its opposite upper end and having a central through bore and annular chamber surrounding said through bore for receiving denture casting material to secure the abutment member to a denture;
   securing means for insertion in said through bore to releasably secure the abutment member to an implant member; and
   an impression cap member for releasably securing to the open upper end of the abutment member, the cap member including means for sealing the internal volume of the abutment member.

2. The system as claimed in claim wherein said securing means includes first temporary securing means for releasably securing said abutment member to an implant member during impression taking, and a second final securing means for securing the abutment member and attached denture to the implant member.

3. The system as claimed in claim 2, wherein said final securing means comprises a fixation screw for attaching said abutment member to said implant member and anti-rotation means for preventing rotation of said fixation screw.

4. The system as claimed in claim wherein said abutment member comprises a generally cylindrical member having an outer diameter at said base end matching that of said implant member mating end, the member having spaced inner and outer walls projecting from said base end to form said annular chamber.

5. The system as claimed in claim 4, wherein the opposing inner and outer surfaces of said outer and inner walls, respectively, have retention grooves for receiving casting material poured into said internal volume.

6. The system as claimed in claim 4, wherein the outer wall is shorter than said inner wall.

7. The system as claimed in claim 4, wherein the outer surface of said outer wall is a polished, smooth surface, the system further including an outer protective sleeve for releasable sliding engagement over said outer wall.

8. The system as claimed in claim 4, wherein said outer wall tapers outwardly from said base end towards said upper end to form a generally V-shaped annular internal volume extending from said base end towards the upper end of said member.

9. The system as claimed in claim 8, wherein said cap member includes an upper part of outer dimensions substantially matching those of the outer wall of said abutment member, and a downwardly extending annular projection for mating engagement with said annular internal volume of said abutment member.

10. The system as claimed in claim 4, wherein said outer wall is shorter than said inner wall, said cap member having a through bore for mating engagement over said inner wall, and projecting filler means for extending into and filling the internal volume between said inner and outer walls.

11. The system as claimed in claim 4, wherein said abutment member through bore is of stepped diameter, including an enlarged diameter portion extending from said open end, a reduced diameter intermediate portion, and a mating end portion matching the shape of a projecting end portion of an insert member to which it is to be attached, the securing means comprises a temporary fixation screw member having an elongate head portion of length greater than said enlarged diameter portion, and a shaft portion extending from said head portion and having outer securing means for securing to corresponding internal securing means in said implant member.

12. The system as claimed in claim 11, wherein said securing means further comprises a final fixation screw having a shorter head portion, and anti-rotation means for fitting into said enlarged bore portion above said fixation screw head, the anti-rotation means having means for coupling to the upper end of said fixation screw and means for engaging with the inner surface of said bore portion to resist rotation of said anti-rotation means and attached fixation screw.

13. The system as claimed in claim 1, wherein said cap member includes orientation means on its outer peripheral surface for producing a correspondingly shaped orientation marking in an impression made over said cap member and abutment member.

14. The system as claimed in claim 13, wherein said orientation means comprises a flat on the outer peripheral surface of said cap member.

15. A method of forming and attaching a denture to one or more implant members installed in a patient's jaw, comprising the steps of:
temporarily securing a mating, abutment base end of an abutment member to a matching, upper mating end of an installed implant member;
releasably securing an impression cap to an open upper end of the abutment member to cover and seal an internal volume of the abutment member;
taking an impression of the patient's jaw in the area of the implant around the abutment member and impression cap;
releasing the abutment member from the implant member;
removing the impression and attached abutment member from the patient's mouth;
attaching an analogue of the implant member to the abutment member;
casting material around the impression, abutment member and attached analogue to form a working cast of the patient's jaw with the implant location;
removing the impression and impression cap from the abutment member;
forming a desired restorative structure and attaching it to the abutment member with portions of the restorative structure extending into the internal volume;
releasing the abutment member and restorative structure from the implant analogue; and
attaching the abutment member and restorative structure to the implant member in the patient's mouth.

16. The method as claimed in claim 15, wherein the step of forming and attaching the restorative structure comprises casting denture material directly around and into the internal volume of the abutment member.

17. The method as claimed in claim 15, wherein the step of forming and attaching the restorative structure comprises forming a pattern of the desired restorative structure around the abutment member, using the pattern to form a cast of the restorative structure separate from the abutment member, and attaching the cast to the abutment member.

18. The method as claimed in claim 15, including a step of cutting an outer wall of the abutment member so that its upper edge follows the contour of the gum line surrounding the implant site in the working cast.

19. The method as claimed in claim 15, wherein the step of attaching the abutment member and restorative structure to the implant member comprises inserting a securing device through a central through bore in the implant member to secure the abutment member to the implant member, and inserting a filler member in the exposed, upper end of the through bore with the upper end of the filler member machined to follow the contour of the upper surface of the restorative structure.

* * * * *

UNITED STATES PATENT AND TRADEMARK OFFICE
CERTIFICATE OF CORRECTION

PATENT NO. : 5,106,300

DATED : April 21, 1992

INVENTOR(S) : ANTON J. VOITIK

It is certified that error appears in the above-identified patent and that said Letters Patent is hereby corrected as shown below:

Column 8, Line 54 after "claim" insert --"1"--

Column 8, Line 65 after "claim" insert --"1"--

Signed and Sealed this

Third Day of August, 1993

Attest:

MICHAEL K. KIRK

Attesting Officer

Acting Commissioner of Patents and Trademarks